US006508869B2

(12) United States Patent
Tseng et al.

(10) Patent No.: US 6,508,869 B2
(45) Date of Patent: Jan. 21, 2003

(54) BORON COMPOUND/AMINE OXIDE COMPOSITIONS

(75) Inventors: Chuen-Ing Tseng, Lawrenceville, NJ (US); Leigh E. Walker, Macungie, PA (US); Charles Conrad Kempinska, Jr., Lake Hiawatha, NJ (US)

(73) Assignee: Lonza Inc., Annandale, NJ (US)

( * ) Notice: Subject to any disclaimer, the term of this patent is extended or adjusted under 35 U.S.C. 154(b) by 0 days.

(21) Appl. No.: 09/897,752

(22) Filed: Jun. 29, 2001

(65) Prior Publication Data

US 2002/0065206 A1 May 30, 2002

Related U.S. Application Data

(60) Provisional application No. 60/215,571, filed on Jun. 30, 2000.

(51) Int. Cl.[7] .............................. C09D 5/00; C09D 5/20
(52) U.S. Cl. ........................ 106/2; 106/18.3; 106/18.32
(58) Field of Search ................................. 510/373, 378, 510/503, 506; 106/2, 18.3, 18.32

(56) References Cited

U.S. PATENT DOCUMENTS

| | | | |
|---|---|---|---|
| 3,296,145 A | 1/1967 | Findlan et al. ............... 252/106 |
| 3,484,523 A | 12/1969 | Findlan et al. ............... 424/248 |
| 3,527,593 A | 9/1970 | Coles et al. .................... 71/94 |
| 3,761,488 A | 9/1973 | Lewis et al. ................. 260/302 |
| 4,005,193 A | 1/1977 | Green et al. ................. 424/168 |
| 4,105,431 A | 8/1978 | Lewis et al. .................... 71/67 |
| 4,179,504 A | 12/1979 | Lynch et al. |
| 4,379,810 A | 4/1983 | Amundsen et al. .......... 428/541 |
| 4,382,105 A | 5/1983 | Amundsen et al. .......... 427/370 |
| 4,526,699 A | * 7/1985 | Jones et al. .................... 252/99 |
| 4,622,248 A | 11/1986 | Leach et al. ................. 427/440 |
| 4,857,322 A | 8/1989 | Goettsche et al. ........... 424/633 |
| 4,929,454 A | 5/1990 | Findlay et al. ............... 424/464 |
| 4,937,143 A | 6/1990 | West ........................ 427/419.8 |
| 4,950,685 A | 8/1990 | Ward ............................ 514/479 |
| 5,061,798 A | 10/1991 | Malouf et al. .................. 514/64 |
| 5,073,570 A | 12/1991 | Tseng .......................... 514/533 |
| 5,276,029 A | 1/1994 | Goettsche et al. ........ 514/231.2 |
| 5,304,237 A | * 4/1994 | Barth et al. ................. 106/18.3 |
| 5,426,121 A | 6/1995 | Bell ............................. 514/500 |
| 5,468,284 A | 11/1995 | Sturm ............................ 106/2 |
| 5,500,153 A | * 3/1996 | Figueroa et al. ............. 252/548 |
| 5,527,384 A | 6/1996 | Williams et al. .......... 106/18.32 |
| 5,536,505 A | 7/1996 | Yu ............................ 106/18.33 |
| H1635 H | * 3/1997 | Vander Meer ............... 510/220 |
| 5,641,726 A | 6/1997 | Walker ......................... 504/158 |
| 5,833,741 A | 11/1998 | Walker ............................ 106/2 |
| 5,858,921 A | 1/1999 | Magin et al. ................. 504/206 |
| 5,891,836 A | * 4/1999 | Kacher ........................ 510/237 |
| 5,929,016 A | * 7/1999 | Harrison ...................... 510/384 |
| 6,037,316 A | * 3/2000 | Garner et al. ................ 510/238 |
| 6,080,715 A | * 6/2000 | Bianchi et al. .............. 510/444 |
| 6,159,924 A | * 12/2000 | Weller et al. ................ 510/384 |
| 6,395,698 B1 | 5/2002 | Daun et al. .................. 510/384 |
| 6,416,789 B1 | 7/2002 | Marks et al. ................. 424/641 |

FOREIGN PATENT DOCUMENTS

| | | | |
|---|---|---|---|
| CA | 1 174 005 | 9/1984 | .......... A01N/31/14 |
| DE | 3743 821 A1 | 7/1989 | ............ B27K/3/34 |
| DE | 4217 882 A1 | 12/1993 | .......... A01N/55/04 |
| DE | 44 41 674 A1 | 5/1996 | ......... C07C/275/32 |
| DE | 0 242 753 | 10/1997 | ............ B27K/3/52 |
| DE | 196 40 874 | 4/1998 | ............ B27K/3/34 |
| DE | 196 48 888 A1 | 5/1998 | ............ B27K/3/50 |
| EP | 0 370 182 | 5/1990 | ............ B27K/3/50 |
| EP | 0 381 482 | 8/1990 | ............ B27K/3/50 |
| EP | 0 571 846 A1 | 12/1993 | .......... A01N/47/12 |
| JP | 57022003 | 2/1982 | ............ B27K/3/52 |
| JP | 64/1796 | 1/1989 | ............ C11D/3/28 |
| JP | 1-268605 | 10/1989 | .......... A01N/33/24 |
| WO | 97/01423 | 1/1997 | ............ B27K/3/50 |
| WO | 98/00008 | 1/1998 | .......... A01N/25/02 |
| WO | 98/18321 | 5/1998 | .......... A01N/25/30 |
| WO | 98/31518 | 7/1998 | ............ B27K/3/00 |

OTHER PUBLICATIONS

American Wood Preservers' Association, P5– Waterborne Preservatives, 4–5, 1998.
Encyclopedia of Chemical Technology, vol. 2, pp. 259–271, John Wiley & Sons Inc., 1978.
Archer et al., Forest Products Journal, 45(1):86–89, Jan. 1995.
Hirobumi et al., 120:301698 1993 (abstract).
Liu et al., 25th Annual Meeting of the International Research Group on Wood Preservation, Nusa Dua Bali, Indonesia, May 29, 1994–Jun. 3, 1994.
Nicholas et al., 28th Annual Meeting of the International Research Group on Wood Preservation, Whistler, Canada, May 25, 1997–May 30, 1997.
Williams et al., American Wood–Preservers' Association, 90:156–176, 1994.
Morris and Byrne, Forest Products Journal, 47(4):71–73, Apr. 1997.

* cited by examiner

*Primary Examiner*—Gregory Delcotto
(74) *Attorney, Agent, or Firm*—Darby & Darby

(57) ABSTRACT

The present invention provides a composition comprising an amine oxide and a boron compound. The boron compound may be boric acid, diboron tetrahydroxide, a borate, a boron oxide, a borane, or any combination of any of the foregoing. Another embodiment of the present invention is a method for preserving and/or waterproofing a wood substrate by contacting the composition with the wood substrate. Yet another embodiment of the present invention is a method for controlling plants, insects, or fungi or regulating the growth of plants comprising applying an insecticidal, herbicidal, fungicidal, or plant growth regulating effective amount of a composition of the present invention to the plants, fungi, insects, the seeds of the plants, or the area on which the plants or fungi grow.

26 Claims, No Drawings

BORON COMPOUND/AMINE OXIDE COMPOSITIONS

The present application claims priority to U.S. Provisional Application No. 60/215,571, Jun. 30, 2000, which is herein incorporated by reference in its entirety.

FIELD OF THE INVENTION

This invention relates to wood preservative and waterproofing compositions and insecticidal, herbicidal, fungicidal, and plant growth regulating compositions containing an amine oxide and a boron compound.

BACKGROUND OF THE INVENTION

Many boron compounds, including borates, are known to be effective as wood preservatives. However, since borates are water soluble, they often leach out of wood substrates resulting in increased susceptibility to insects and fungi.

Various boron compounds are also known to be effective as insecticides, herbicides, fungicides, and plant growth regulating agents. These compounds, however, often do not disperse well when applied to plants and fungi. Therefore, greater concentrations of borates are frequently incorporated into such compositions.

There is a continuing need for improved boron compound containing wood preservatives and waterproofing compositions which have improved leach resistance and improved penetration and distribution into wood substrates. Also, there is a need for boron compound containing insecticidal, herbicidal, fungicidal, and plant growth regulating compositions which improve the efficacy of the boron compound and improve the dispersion of the boron compound when applied to plants and fungi.

SUMMARY OF THE INVENTION

Applicants have discovered that amine oxides enhance the performance of boron compounds as wood preservatives, provide waterproofing properties, and improve the leach resistance of wood substrates to which they are applied. Also, amine oxides improve the efficacy of boron compounds as insecticides, herbicides, fungicides, and plant growth regulating agents and provide better dispersion of the boron compounds when applied to plants and fungi. The present invention provides a composition comprising an amine oxide and a boron compound. Preferred amine oxides include, but are not limited to, dodecyldimethylamine oxide, tridecyldimethylamine oxide, tetradecyldimethyl amine oxide, pentadecyldimethylamine oxide, or hexadecyldimethylamine oxide. The boron compound may be boric acid, diboron tetrahydroxide, a borate, a boron oxide, a borane or any combination of the foregoing. Preferably, the composition comprises boric acid, a borate, a salt of a borate, or a mixture of boric acid and a borate or a salt thereof.

Another embodiment of the present invention is a method for preserving and/or waterproofing a wood substrate by contacting the composition with the wood substrate.

Yet another embodiment is an article comprising a wood substrate and the composition of the present invention.

According to another embodiment of the invention, a method for controlling plants, insects, or fungi or regulating the growth of plants is provided comprising applying an insecticidal, herbicidal, fungicidal, or plant growth regulating effective amount of the composition of the present invention to the plants, fungi, insects, the seeds of the plants, or the area on which the plants or fungi grow.

DETAILED DESCRIPTION OF THE INVENTION

The present invention provides a composition comprising an amine oxide and a boron compound. The amine oxide enhances penetration of the boron compound into wood substrates and improves leach resistance. Also, the amine oxide enhances the efficacy of the boron compound as an insecticide, herbicide, fungicide, and plant growth regulating agent. The compositions of the present invention have high water solubility and/or dispersibility and low volatility.

The amine oxide may be a trialkylamine oxide; an alkylcyclicamine oxide; a dialkylpiperazine di-N-oxide; an alkyldi(ethoxylated oxyalkyl)amine oxide; a dialkylbenzylamine oxide; a fatty dimethylaminopropylamine oxide; a diamine oxide; a triamine oxide; and any combination of any of the foregoing.

Preferred trialkylamine oxides have the formula $R^1R^2R^3N\rightarrow O$, where $R^1$ is a linear, branched, cyclic or any combination thereof $C_8$ to $C_{40}$ saturated or unsaturated group; and $R^2$ and $R^3$ independently are linear, branched, or any combination thereof $C_1$ to $C_{40}$ saturated or unsaturated groups. $R^1$, $R^2$, and $R^3$ independently may be alkyl, alkenyl, or alkynyl groups. More preferably, $R^1$ is a linear, branched, cyclic or any combination thereof $C_8$ to $C_{22}$ saturated or unsaturated group, such as coco, hydrogenated tallow, soya, decyl, and hexadecyl; and $R^2$ and $R^3$ independently are linear, branched, or any combination thereof $C_1$ to $C_{22}$ saturated or unsaturated groups, such as coco, hydrogenated tallow, soya, decyl, and hexadecyl.

A preferred trialkylamine oxide is a dialkylmethylamine oxide having the formula $R^1R^2CH_3N\rightarrow O$, where $R^1$ and $R^2$ are defined as above. Another preferred trialkylamine oxide is an alkyldimethylamine oxide having the formula $R^1(CH_3)_2N\rightarrow O$, where $R^1$ is defined as above. Suitable alkyldimethylamine oxides include, but are not limited to, a $C_{10}$ alkyldimethylamine oxide, a $C_{12}-C_{14}$ alkyldimethylamine oxide, a $C_{16}-C_{18}$ alkyldimethylamine oxide, and any combination of any of the foregoing. According to a preferred embodiment, the alkyldimethyl amine oxide is a $C_{12}-C_{16}$ alkyldimethyl amine oxide and more preferably a $C_{12}$ or $C_{16}$ alkyldimethyl amine oxide.

Preferred alkylcyclicamines oxide have the formula $R^4R^5R^6N\rightarrow O$ where $R^4$ is defined as $R^1$ above and $R^5$ and $R^6$ are linked to form a cyclic group. The cyclic group typically contains from about 4 to about 10 carbon atoms and may optionally contain oxygen, sulfur, nitrogen, or any combination of any of the foregoing. More preferred alkylcyclicamine oxides include, but are not limited to, an alkylmorpholine-oxide, a dialkylpiperazine di-N-oxide, and any combination of any of the foregoing.

Preferred alkylmorpholine-oxides have the formula

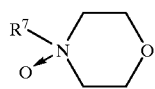

where $R^7$ is defined as $R^1$ above.

Preferred dialkylpiperazine di-N-oxides have the formula

where $R^8$ is defined as $R^1$ above and $R^9$ is defined as $R^2$ above.

Preferred alkyldi(ethoxylated oxyalkyl)amine oxides have the formula

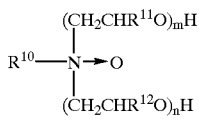

where $R^{10}$ is defined as $R^1$ above; $R^{11}$ and $R^{12}$ independently are H or $CH_3$; and m and n independently are integers from about 1 to about 10.

Preferred dialkylbenzylamine oxides have the formula $R^{13}R^{14}R^{15}N \rightarrow O$, where $R^{13}$ is defined as $R^1$ above; $R^{14}$ is defined as $R^2$ above; and $R^{15}$ is benzyl. More preferred dialkylbenzylamine oxides include, but are not limited to, alkylbenzylmethylamine oxides having the formula $R^{13}R^{15}CH_3N-O$ where $R^{13}$ and $R^{15}$ are defined as above.

Preferred fatty dimethylaminopropylamine oxides have the formula

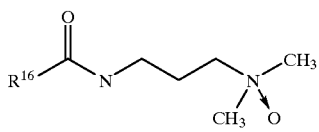

where $R^{16}$ is defined as $R^1$ above.

Preferred diamine oxides have the formula

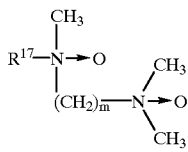

where $R^{17}$ is defined as $R^1$ above; and m is an integer from about 1 to about 10.

Preferred triamine oxides have the formula

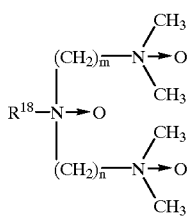

where $R^{18}$ is defined as $R^1$ above; and m and n independently are integers from about 1 to about 10.

Long chain ($C_{16}$ or greater) amine oxides, such as hexadecylamine oxides and hydrogenated tallow amine oxides, are particularly preferable for imparting waterproofing properties to the composition. Short chain ($C_{14}$ and shorter) amine oxides aid in solubilizing the boron compound and long chain amine oxides.

The boron compound may be boric acid, diboron tetrahydroxide, a borate, a boron oxide, a borane, or any combination of any of the foregoing. Suitable boron compounds, include, but are not limited to, boranes and borate esters that produce oxides of boron in aqueous media. In a preferred embodiment, the boron compound is boric acid, a borate (e.g., basic sodium borate (borax)), or a mixture of boric acid and a borate.

Suitable borates include, but are not limited to, perborates, metaborates, tetraborates, octaborates, borate esters, and any combination of any of the foregoing. Preferred borates include, but are not limited to, metallic borates (e.g., sodium borate, zinc borate and potassium borate), such as disodium tetraborate decahydrate, disodium octaborate tetrahydrate, sodium metaborate, sodium perborate monohydrate, disodium octaborate, sodium tetraborate pentahydrate, sodium tetraborate, copper metaborate, zinc borate, barium metaborate, and any combination of any of the foregoing; bis(2-aminoethyl) borate; and any combination of any of the foregoing. More preferably, the borate is disodium octaborate tetrahydrate, available as Tim-Bor™ from U.S. Borax Inc. of Valencia, Calif. A preferred boron oxide is boric oxide.

The composition may include a solvent, such as water and water miscible solvents, including, but not limited to, alcohols; glycols, such as ethylene glycol; esters; ethers; polyethers; and any combination of any of the foregoing. Compositions of the present invention containing boranes and/or borate esters preferably also contain water in order to hydrolyze them to produce oxides of boron.

The weight ratio of amine oxide to boron compound broadly ranges from about 1:50 to about 50:1 and preferably from about 1:5 to 5:1.

According to one embodiment of the invention, the composition in concentrated form contains broadly from about 1 to about 100%, preferably from about 10 to about 30%, and more preferably from about 10 to about 30% by weight of combined amine oxide and boron compound based upon 100% weight of total composition.

Wood preservative and/or waterproofing use dilutions of the composition typically comprise a biocidally effective amount of boron compound and a preservative enhancing and/or waterproofing effective amount of the amine oxide. Wood preservative and/or waterproofing use dilutions preferably comprise from about 0.5 to about 2% by weight of amine oxide and from about 0.5 to about 2% by weight of boron compound based upon 100% weight of total composition.

Insecticidal, herbicidal, fungicidal, and/or plant growth regulating use dilutions of the composition typically comprise an insecticidal, herbicidal, fungicidal, and/or plant growth regulating effective amount of the boron compound and an insecticidal, herbicidal, fungicidal, and/or plant growth regulating enhancing effective amount of the amine oxide. Insecticidal, herbicidal, fungicidal, and/or plant growth regulating use dilutions preferably comprise from about 0.01 to about 10% by weight of amine oxide and from about 0.01 to about 5% by weight of boron compound based upon 100% weight of total use dilution.

Other adjuvants may be included in the composition as known to one of ordinary skill in the art.

Another embodiment of the present invention is a method for preserving and/or waterproofing a wood substrate by contacting the composition of the present invention with the wood substrate. The composition may be applied to the wood substrate by any method known to one of ordinary skill in the art including, but not limited to, brushing, dipping, soaking, vacuum impregnation, and pressure treatment using various cycles.

Yet another embodiment of the present invention is a method for controlling plants, insects, or fungi or regulating the growth of plants comprising applying an insecticidal, herbicidal, fungicidal, or plant growth regulating effective amount of the composition of the present invention to the plants, fungi, insects, the seeds of the plants, or the area on which the plants or fungi grow. The composition of the present invention may be applied to the plants, fungi, insects, the seeds of the plants, or the area on which the plants or fungi grow by any method known to one of ordinary skill in the art including, but not limited to, spraying.

Generally the composition of the present invention is applied at a rate ranging from about 1 to about 1,000 g/ha (grams/hectare) to plants or fungi, the seeds of the plants, and/or the area on which the plants or fungi grow.

The composition of the present invention may be prepared by mixing the boron compound, amine oxide, solvents, and adjuvants. The mixture may be heated and/or stirred to expedite mixing.

The following example illustrates the invention without limitation. All parts and percentages are given by weight unless otherwise indicated. The abbreviation "DMAO" stands for dimethylamine oxide.

EXAMPLE

Evaluation of Penetration of Borate-Amine Oxide Formulations

Pieces of permeable southern pine, impermeable Douglas Fir, and intermediately permeable Hem-Fir were treated with solutions containing (i) 2 or 5% by weight of a boron compound (i.e., Tim-Bor™, borax or boric acid) and optionally (ii) 0.4 or 1% by weight of Barlox® 12 or a mixture of Barlox® 16S and Barlox® 12. Tim-Bor™ is a 98% solution of disodium octaborate tetrahydrate available from U.S. Borax Inc. of Valencia, Calif. Barlox® 12 is an aqueous solution containing 30% by weight of dodecyldimethylamine oxide available from Lonza Inc. of Fair Lawn, N.J. Barlox® 16S is an aqueous solution containing 30% by weight of hexadecyl dimethylamine oxide available from Lonza Inc.

End-matched samples of each type of wood were prepared by cutting 2" by 4" boards into 8" lengths. One end of each sample was coated with epoxy to preclude penetration of the treating solutions.

The samples were treated with the solutions by either dipping them into the solution or by vacuum impregnation as indicated in Tables 1 through 4 below. Immediately after treatment, the samples were cut in half and sprayed with an indicator solution, which was a mixture of curcumin and salicylic acid, to monitor borate penetration. The penetration was measured. At weekly intervals thereafter, approximately ⅛" was removed from the cut ends of the samples and penetration was reevaluated with the indicator spray. In some cases, the indicator spray gave very light, diffuse color changes that were difficult to interpret.

The treating solutions tested and their results are shown in Tables 1 through 4 below.

TABLE 1

| Treating Solution | Species of Wood | Penetration (mm) at Day | | | | |
|---|---|---|---|---|---|---|
| | | 0 | 8 | 14 | 22 | 29 |
| 2% Borax | Southern Pine | 2 | 10 | 11 | 12 | 15 |
| 2% Borax and 0.4% Dodecyl DMAO | Southern Pine | 2 | 10 | 19 | 19 | 19 |
| 2% Borax and 0.4% of total Dodecyl DMAO and Hexadecyl DMAO (at a weight ratio of 2:5) | Southern Pine | 1 | 12 | 19 | 19 | 19 |
| 2% Boric Acid | Hem-Fir | 0 | 5 | 6 | 7 | 7 |
| 2% Boric Acid and 0.4% Dodecyl DMAO | Hem-Fir | 1 | 6 | 7 | 9 | 8 |
| 2% Boric Acid - Bx16/12 | Hem-Fir | 2 | 7 | 8 | 9 | 9 |
| 2% Tim-Bor ® (active) | Douglas Fir | 4 | 5 | 4 | 7 | 8 |
| 2% Tim-Bor ® (active) and 0.4% Dodecyl DMAO | Douglas Fir | 2 | 5 | 7 | 9 | 8 |
| 2% Tim-Bor ® and 0.4% of total Dodecyl DMAO and Hexadecyl DMAO (at a weight ratio of 2:5) | Douglas Fir | 0 | 3 | 2 | 3 | 3 |

For Tables 2 through 4 below, the following abbreviations have the following definitions:

BX—Aqueous solution containing 2% borax.

BXA1—Aqueous solution containing 2% borax and 0.4% dodecyl DMAO.

BXA2—Aqueous solution containing 2% borax and 0.4% of total dodecyl DMAO and hexadecyl DMAO at a weight ratio of 2:5.

5%-BX—Aqueous solution containing 5% borax.

5%-BXA1—Aqueous solution containing 5% borax and 1% dodecyl DMAO.

5%-BXA2—Aqueous solution containing 5% borax and 1% of total dodecyl DMAO and hexadecyl DMAO at a weight ratio of 2:5.

TB—Aqueous solution containing 2% Tim-Bor® (active).

TBA1—Aqueous solution containing 2% Tim-Bor® and 0.4% dodecyl DMAO.

TBA2—Aqueous solution containing 2% Tim-Bor® and 0.4% of total dodecyl DMAO and hexadecyl DMAO at a weight ratio of 2:5.

H—Aqueous solution containing 2% boric acid.

HA1—Aqueous solution containing 2% boric acid and 0.4% dodecyl DMAO.

HA2—Aqueous solution containing 2% boric acid and 0.4% of total dodecyl DMAO and hexadecyl DMAO at a weight ratio of 2:5.

NV—Not Visible

?—Questionable due to lightness

TABLE 2

Penetration Results (mm) for Southern Pine

| Treating Solution | Treatment Type | Treatment Time (min) | Penetration (mm) at Day | | | | |
|---|---|---|---|---|---|---|---|
| | | | 0 | 8 | 14 | 22 | 29 |
| 5%-BXA1 | Vacuum | 10 | 2 | 10 | All | 14 | All |
| 5%-BX | Vacuum | 10 | 2 | 10 | 11 | 12 | 15 |
| 5%-BXA2 | Vacuum | 10 | 1 | 12 | All | All | All |
| 5%-BXA1 | Vacuum | 10 | 3 | 10 | 8 | 14 | 15 |
| 5%-BX | Vacuum | 10 | 3 | 6 | 7 | 12 | 11 |

TABLE 2-continued

Penetration Results (mm) for Southern Pine

| Treating Solution | Treatment Type | Treatment Time (min) | Penetration (mm) at Day | | | | |
|---|---|---|---|---|---|---|---|
| | | | 0 | 8 | 14 | 22 | 29 |
| 5%-BXA2 | Vacuum | 10 | 2 | 8 | 9 | 13 | 15 |
| BXA1 | Vacuum | 10 | 4 | 7 | 6 | 12 | 10 |
| BX | Vacuum | 10 | 7 | 10 | 11 | 13 | 14 |
| BX | Vacuum | 10 | 3 | 5 | 6 | 7 | 9 |
| BXA2 | Vacuum | 10 | 7 | 8 | 9 | 11 | 11 |
| BXA1 | Dip | 6 | NV | NV | NV | — | — |
| BXA1 | Dip | 6 | NV | NV | NV | — | — |
| BXA1 | Dip | 6 | NV | NV | NV | — | — |
| BXA1 | Dip | 30 | NV | NV | NV | NV | NV |
| TBA1 | Vacuum | 10 | 4 | 6 | 6 | 9 | 7 |
| TB | Vacuum | 10 | 3 | 10 | 9 | All? | 12 |
| TBA2 | Vacuum | 10 | 3 | 7 | 6 | 10 | 11 |
| TBA1 | Dip | 3 | NV | NV | NV | — | — |
| TB | Dip | 3 | NV | NV | 3? | — | — |
| TBA1 | Dip | 6 | NV | NV | NV | — | — |
| TB | Dip | 6 | NV | 3 | NV | — | — |
| TBA1 | Dip | 30 | NV2 | NV | NV | 2 | 2 |
| TBA2 | Dip | 30 | | 5 | 4 | 6 | 7 |
| HA1 | Vacuum | 10 | 5 | 10 | 12 | 13 | 13 |
| H | Vacuum | 10 | 9 | 9 | All | All | All |
| HA2 | Vacuum | 10 | 5 | 10 | 9 | 11 | 11 |
| HA1 | Dip | 6 | NV | NV | NV | — | — |
| H | Dip | 6 | NV | NV | NV | — | — |
| HA2 | Dip | 6 | NV | NV | NV | — | — |

TABLE 3

Penetration Results (mm) for Douglas Fir

| Treating Solution | Treatment Type | Treatment Time (min) | Penetration (mm) at Day | | | | |
|---|---|---|---|---|---|---|---|
| | | | 0 | 8 | 14 | 22 | 29 |
| BXA1 | Vacuum | 10 | NV | 1 | 2 | 3 | 3 |
| BX | Vacuum | 10 | 3 | 2 | 2 | 3 | 3 |
| BX | Vacuum | 10 | NV | 2 | 2 | 3 | All? |
| BXA2 | Vacuum | 10 | 3 | 2 | 2 | 3 | 3 |
| BXA1 | Dip | 6 | NV | 3 | 2 | 9 | 8 |
| BXA1 | Dip | 6 | NV | 1 | 5 | 9 | 7 |
| BXA1 | Dip | 6 | 1 | 4 | 5 | 9 | 8 |
| BXA1 | Dip | 30 | 2 | 4 | 6 | All? | 10 |
| TBA1 | Vacuum | 10 | NV | 2 | 2 | 3 | 4 |
| TB | Vacuum | 10 | NV | 3 | 2 | 4 | 4 |
| TBA2 | Vacuum | 10 | NV | 3 | 3 | 3 | 4 |
| TBA1 | Dip | 3 | 4 | 5 | 4 | 7 | 7 |
| TB | Dip | 3 | NV | 2 | 4 | 7 | 8 |
| TBA1 | Dip | 6 | NV | 7 | 5 | 7 | 7 |
| TB | Dip | 6 | 2 | 4 | 5 | 7 | 8 |
| TBA1 | Dip | 30 | 2 | 5 | 7 | 9 | 8 |
| TBA2 | Dip | 30 | NV | 3 | 2 | 3 | 3 |
| HA1 | Vacuum | 10 | NV | 4 | 3 | 3 | 3 |
| H | Vacuum | 10 | NV | 2 | 3 | 4 | 3 |
| HA2 | Vacuum | 10 | NV | 3 | 3 | 4 | 3 |
| HA1 | Dip | 6 | NV | 2 | 2 | 8 | 8 |
| H | Dip | 6 | 2 | 5 | 4 | 9 | 8 |
| HA2 | Dip | 6 | NV | 7 | 5 | 10 | 8 |

TABLE 4

Sample Penetration Results (mm) for Hem-Fir

| Treating Solution | Treatment Type | Treatment Time (mm) | Penetration (mm) at Day | | | | |
|---|---|---|---|---|---|---|---|
| | | | 0 | 8 | 14 | 22 | 29 |
| BXA1 | Vacuum | 10 | 1 | 4 | 5 | 3 | 4 |
| BX | Vacuum | 10 | 2 | 4 | 4 | 4 | 4 |
| BX | Vacuum | 10 | 2 | 4 | 4 | 4 | 3 |

TABLE 4-continued

Sample Penetration Results (mm) for Hem-Fir

| Treating Solution | Treatment Type | Treatment Time (mm) | Penetration (mm) at Day | | | | |
|---|---|---|---|---|---|---|---|
| | | | 0 | 8 | 14 | 22 | 29 |
| BXA2 | Vacuum | 10 | NV | 2 | 3 | 3 | 3 |
| BXA1 | Dip | 6 | NV | NV | NV | — | — |
| BXA1 | Dip | 6 | NV | NV | NV | — | — |
| BXA1 | Dip | 6 | NV | NV | NV | — | — |
| BXA1 | Dip | 30 | NV | NV | 10 | All? | All? |
| TBA1 | Vacuum | 10 | NV | 1 | 2 | 5 | 3 |
| TB | Vacuum | 10 | 1 | 3 | 3 | 6 | 4 |
| TBA2 | Vacuum | 10 | NV | 4 | 4 | 6 | 3 |
| TBA1 | Dip | 3 | NV | NV | 3 | All? | All? |
| TB | Dip | 3 | NV | NV | 3 | All? | All? |
| TBA1 | Dip | 6 | NV | NV | 3 | 10 | 10 |
| TB | Dip | 6 | NV | 5? | 6 | 10 | 10 |
| TBA1 | Dip | 30 | NV | NV | 4 | All? | All? |
| TBA2 | Dip | 30 | NV | 3 | 3 | 8 | 6 |
| HA1 | Vacuum | 10 | 1 | 6 | 7 | 9 | 8 |
| H | Vacuum | 10 | 1 | 5 | 6 | 7 | 7 |
| HA2 | Vacuum | 10 | 2 | 7 | 8 | 9 | 9 |
| HA1 | Dip | 6 | NV | NV | 5 | All? | All? |
| H | Dip | 6 | NV | 7 | 5 | All? | All? |
| HA2 | Dip | 6 | NV | 1 | 6 | All? | All? |

All patents, applications, articles, publications, and test methods mentioned above are hereby incorporated by reference.

Many variations of the present invention will suggest themselves to those skilled in the art in light oft he above detailed description. Such obvious variations are within the full intended scope of the appended claims.

We claim:

1. A wood preservative and/or waterproofing composition comprising
   (A) a trialkylamine oxide; and
   (B) a boron compound selected from the group consisting of diboron tetrahydroxide, octaborate, borate esters, bis(2-aminoethyl) borate, a borane, disodium octaborate tetrahydrate, disodium octaborate, sodium tetraborate pentahydrate, copper metaborate, zinc borate, barium metaborate, bis(2-aminoethyl)borate, and any combination of any of the foregoing.

2. A composition as defined in claim 1, wherein said trialkylamine oxide has the formula $R^1R^2R^3N \rightarrow O$, wherein $R^1$ is a linear, branched, cyclic or any combination thereof $C_8$ to $C_{40}$ saturated or unsaturated group; and $R^2$ and $R^3$ independently are linear, branched, or any combination thereof $C_1$ to $C_{40}$ saturated or unsaturated groups.

3. A composition as defined in claim 2, wherein $R^1$ is a linear, branched, cyclic or any combination thereof $C_8$ to $C_{22}$ saturated or unsaturated group; and $R^2$ and $R^3$ independently are linear, branched, or any combination thereof $C_1$ to $C_{22}$ saturated or unsaturated groups.

4. A composition as defined in claim 3, wherein $R^2$ and $R^3$ independently are linear, branched, or any combination thereof $C_8$ to $C_{22}$ saturated or unsaturated groups.

5. A composition as defined in claim 2, wherein said trialkylamine oxide is a dialkylmethylamine oxide having the formula $R^1R^2CH_3N \rightarrow O$, wherein $R^1$ is a linear, branched, cyclic or any combination thereof $C_8$ to $C_{40}$ saturated or unsaturated group; and $R^2$ is a linear, branched, or any combination thereof $C_1$ to $C_{40}$ saturated or unsaturated group.

6. A composition as defined in claim 5, wherein $R^1$ is a linear, branched, cyclic or any combination thereof $C_8$ to $C_{22}$ saturated or unsaturated group; and $R^2$ is a linear, branched, or any combination thereof $C_1$ to $C_{22}$ saturated or unsaturated group.

7. A composition as defined in claim 2, wherein said trialkylamine oxide is an alkyldimethylamine oxide having the formula $R^1(CH_3)_2N{\rightarrow}O$, wherein $R^1$ is a linear, branched, cyclic or any combination thereof $C_8$ to $C_{40}$ saturated or unsaturated group.

8. A composition as defined in claim 7, wherein $R^1$ is a linear, branched, cyclic or any combination thereof $C_8$ to $C_{22}$ saturated or unsaturated group.

9. A composition as defined in claim 7, wherein said alkyldimethylamine oxide is selected from the group consisting of a $C_{10}$ alkyldimethylamine oxide, $C_{12}$–$C_{14}$ alkyldimethylamine oxide, $C_{16}$–$C_{18}$ alkyldimethylamine oxide, and any combination of any of the foregoing.

10. A composition as defined in claim 1, wherein said boron compound is selected from the group consisting of a metaborate, a tetraborate, an octaborate, a borate ester, and any combination of any of the foregoing.

11. A composition as defined in claim 1, wherein said boron compound is disodium octaborate tetrahydrate.

12. A composition as defined in claim 1, further comprising a solvent.

13. A composition as defined in claim 12, wherein said solvent is water.

14. A composition as defined in claim 12, wherein said solvent is selected from the group consisting of alcohols, glycols, esters, ethers, polyethers, and any combination of any of the foregoing.

15. A composition as defined in claim 14, wherein said solvent comprises ethylene glycol.

16. A composition as defined in claim 1, wherein said composition comprises a biocidally effective amount of said boron compound.

17. A composition as defined in claim 1, wherein said composition comprises an insecticidal, herbicidal, fungicidal, or plant growth regulating effective amount of said boron compound.

18. A composition as defined in claim 1, wherein said composition comprises a preservative enhancing and/or waterproofing effective amount of amine oxide.

19. A composition as defined in claim 1, wherein said composition comprises an insecticidal, herbicidal, fungicidal, or plant growth regulating enhancing effective amount of amine oxide.

20. A composition as defined in claim 1, wherein the weight ratio of said amine oxide to said boron compound ranges from about 1:50 to about 50:1.

21. A composition as defined in claim 20, wherein said weight ratio ranges from about 1:5 to about 5:1.

22. A composition as defined in claim 1, wherein said composition comprises from about 0.01 to about 10% by weight of amine oxide and from about 0.01 to about 5% by weight of boron compound based upon 100% weight of total composition.

23. A composition as defined in claim 1, wherein said composition comprises from about 0.5 to about 2% by weight of amine oxide and from about 0.5 to about 2% by weight of boron compound based upon 100% weight of total composition.

24. A method for preserving a wood substrate, said method comprising contacting said wood substrate with a composition as defined in claim 1.

25. A method for waterproofing a wood substrate, said method comprising contacting said wood substrate with a composition as defined in claim 1.

26. An article comprising (A) a wood substrate; and (B) a composition as defined in claim 1.

* * * * *